United States Patent [19]
Baltz et al.

[11] Patent Number: 6,025,174
[45] Date of Patent: Feb. 15, 2000

[54] GLYCOSYLTRANSFERASE GENE GFTD FROM *AMYCOLATOPSIS ORIENTALIS*

[75] Inventors: Richard H. Baltz; Patricia J. Solenberg, both of Indianapolis, Ind.

[73] Assignee: Eli Lilly and Company, Indianapolis, Ind.

[21] Appl. No.: 09/120,052

[22] Filed: Jul. 21, 1998

Related U.S. Application Data

[62] Division of application No. 08/924,847, Sep. 5, 1997, Pat. No. 5,821,098
[60] Provisional application No. 60/026,028, Sep. 13, 1996, abandoned.

[51] Int. Cl.[7] .............................. C12N 9/10; C12N 15/54
[52] U.S. Cl. ........................................... 435/193; 536/23.2
[58] Field of Search ............................. 435/193; 536/23.2

[56] References Cited

PUBLICATIONS

S. K. Chung, et al. "Biosynthetic Studies f Aridicin Antibiotics: Microbial Transformations and Glycosylations by Protoplasts." *Journal of Antibiotics* 39(5): 652–659 (May 1986).

M. J. Zmijewski, Jr., and B. Briggs. "Biosynthesis of vancomycin: identification of TDP–glucose: aglycosyl–vancomycin glucosyltransferase from *Amycolatopsis orientalis*." *FEMS Microbiology Letters* 5:129–134 (1989).

M. J. Zmijewski, Jr., and J. T. Fayerman. *Genetic and Biochemistry of Antibiotic Production* Ed. L.C. Vining and and C. Stuttard. Butterworth Heinemann, Boston. Chapter 18: "Glycopeptide Antibiotics." pp. 71–83 (1995).

*Primary Examiner*—Rebecca E. Prouty
*Attorney, Agent, or Firm*—Raymond S. Parker III; Thomas D. Webster

[57] ABSTRACT

The invention provides isolated nucleic acid compounds encoding the glycosyltransferase protein GtfD of *Amycolatopsis orientalis*. Also provided are vectors carrying the gtfD gene, transformed heterologous host cells for expressing the GtfD protein, and methods for producing glycopeptide compounds using the cloned gtfD gene.

1 Claim, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1224 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..1224

(xi) SEQUENCE DESCRIPTION: SEQ ID NO:1:

```
ATG CGT GTG TTG TTG TCG GTG TGC GGA ACC CGC GGG GAC GTC GAG ATC      48
Met Arg Val Leu Leu Ser Val Cys Gly Thr Arg Gly Asp Val Glu Ile
 1               5                  10                  15

GCG GTG TCG CTG GCG GTC CGG CTG AAG GCG CTC GGC GTC GGG ACG CGG      96
Ala Val Ser Leu Ala Val Arg Leu Lys Ala Leu Gly Val Gly Thr Arg
             20                  25                  30

ATG TGC GCA CCG CCC GCC GCC GCC GAG CGG CTG GCC GAG GTC GAG GTG     144
Met Cys Ala Pro Pro Ala Ala Ala Glu Arg Leu Ala Glu Val Glu Val
         35                  40                  45

CCG CAT GTG CCG GTC GGC CTT CCG CAG CAC ATG ATG TTG CAG GAG GGG     192
Pro His Val Pro Val Gly Leu Pro Gln His Met Met Leu Gln Glu Gly
 50                  55                  60

ATG CCG CCG CCG CCC CCG GAG GAG GAG CGG CGG CTC GCG GCC ATG ACG     240
Met Pro Pro Pro Pro Pro Glu Glu Glu Arg Arg Leu Ala Ala Met Thr
 65                  70                  75                  80

GTC GAG ATG CAG TTC GAC GCG ATC CCC TCG GCC GCC GAA GGA TGC GTG     288
Val Glu Met Gln Phe Asp Ala Ile Pro Ser Ala Ala Glu Gly Cys Val
                 85                  90                  95

GCG GTG GTG GCG GTC GGC GAT CTG GCC GCC GCG ACC GGC GTG CGG TCG     336
Ala Val Val Ala Val Gly Asp Leu Ala Ala Ala Thr Gly Val Arg Ser
            100                 105                 110

GTG GCC GAA AAG CTG GGC CTC CCC TTC TTC TAC TCC GTC CCG AGC CCG     384
Val Ala Glu Lys Leu Gly Leu Pro Phe Phe Tyr Ser Val Pro Ser Pro
        115                 120                 125

GTC TAC CTG GCT TCC CCG CAC TTC CCG CCG CCC TAT GAC GAG CCG ACC     432
Val Tyr Leu Ala Ser Pro His Phe Pro Pro Pro Tyr Asp Glu Pro Thr
    130                 135                 140

ACC CCG GGC GTG ACC GAC CAC CGG ACA CTG TGG GAA GAG CGT GCC CAC     480
Thr Pro Gly Val Thr Asp His Arg Thr Leu Trp Glu Glu Arg Ala His
145                 150                 155                 160

CGG TTC GCG GAA CGG TAC GGG GAG ACG CTC AAC CGG CGG CGG GCC GCG     528
Arg Phe Ala Glu Arg Tyr Gly Glu Thr Leu Asn Arg Arg Arg Ala Ala
                165                 170                 175

ATC GGC CTG CCG CCG GTG GAG GAC GTC TTC GGC TAC GGC CAC GGC GAC     576
Ile Gly Leu Pro Pro Val Glu Asp Val Phe Gly Tyr Gly His Gly Asp
            180                 185                 190

CGG CCC ATC CTG TCG GCG GAC CCG GTC CTC GCC CCG CTG CAG CCG GAC     624
Arg Pro Ile Leu Ser Ala Asp Pro Val Leu Ala Pro Leu Gln Pro Asp
        195                 200                 205
```

-continued

```
GTC GAC GCC GTG CAG ACC GGC GCG TGG ATC CTG ACC GAC GAC CGG CCG      672
Val Asp Ala Val Gln Thr Gly Ala Trp Ile Leu Thr Asp Asp Arg Pro
    210                 215                 220

CTT CCC CCG GAG CTG GAG GCG TTC CTG GCC GCC GGC CCA CCG CCG GTG      720
Leu Pro Pro Glu Leu Glu Ala Phe Leu Ala Ala Gly Pro Pro Pro Val
225                 230                 235                 240

CAC GTG GGT TTC GGC AGC TCG TCC GGG AAG GGG ATC GCC GAC GCC GCG      768
His Val Gly Phe Gly Ser Ser Ser Gly Lys Gly Ile Ala Asp Ala Ala
                245                 250                 255

AAG ATC GCC GTC GAG GTG AGC CGT GCC CAC GGC CGC CGG GTG ATC CTC      816
Lys Ile Ala Val Glu Val Ser Arg Ala His Gly Arg Arg Val Ile Leu
            260                 265                 270

TCC CGA GGG TGG ACC GAT CTG CTC CTG CCC GAC GAC CGG GAG GAC TGT      864
Ser Arg Gly Trp Thr Asp Leu Leu Leu Pro Asp Asp Arg Glu Asp Cys
        275                 280                 285

TTC GCC ATC GGC GAG GTG AAC TTC CAG GCG CTG TTC CCC CGG GTG GCC      912
Phe Ala Ile Gly Glu Val Asn Phe Gln Ala Leu Phe Pro Arg Val Ala
    290                 295                 300

GCC GTC ATC CAT CAC GGC AGC GCG GGC ACG GAA CAC GTG GCC ACG CGG      960
Ala Val Ile His His Gly Ser Ala Gly Thr Glu His Val Ala Thr Arg
305                 310                 315                 320

GCG GGC GTC CCC CAG CTC GTG ATC CCC CGG AAC ACC GAC CAG CCG TAC     1008
Ala Gly Val Pro Gln Leu Val Ile Pro Arg Asn Thr Asp Gln Pro Tyr
                325                 330                 335

TTC GCC GCC AGG GTT GCC GAT CTG GGG ATC GGT GTG GCG CAC GAC GGC     1056
Phe Ala Ala Arg Val Ala Asp Leu Gly Ile Gly Val Ala His Asp Gly
            340                 345                 350

CCG ACG CCG ACC TTC GAG TCC CTG TCG GCC GCG CTC ACC ACG GTC CTG     1104
Pro Thr Pro Thr Phe Glu Ser Leu Ser Ala Ala Leu Thr Thr Val Leu
        355                 360                 365

GCG CCG GAA ACG CGC GCG CGG GCG CGG GCC GTG GCG GCC ATG GCC CAG     1152
Ala Pro Glu Thr Arg Ala Arg Ala Arg Ala Val Ala Ala Met Ala Gln
    370                 375                 380

ACC GAC GGC GCG GCG GCG GCC GCG GAT CTG GTG CTC GCC GCC GTC GGC     1200
Thr Asp Gly Ala Ala Ala Ala Asp Leu Val Leu Ala Ala Val Gly
385                 390                 395                 400

GGG AAC GAG CCC GCC GTT CCC GCG                                      1224
Gly Asn Glu Pro Ala Val Pro Ala
                405
```

(2) INFORMATION FOR SEQ ID NO:2:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Val Leu Leu Ser Val Cys Gly Thr Arg Gly Asp Val Glu Ile
 1               5                  10                  15

Ala Val Ser Leu Ala Val Arg Leu Lys Ala Leu Gly Val Gly Thr Arg
                20                  25                  30

Met Cys Ala Pro Pro Ala Ala Ala Glu Arg Leu Ala Glu Val Glu Val
            35                  40                  45

Pro His Val Pro Val Gly Leu Pro Gln His Met Met Leu Gln Glu Gly
        50                  55                  60

Met Pro Pro Pro Pro Glu Glu Glu Arg Arg Leu Ala Ala Met Thr
65                  70                  75                  80
```

```
Val Glu Met Gln Phe Asp Ala Ile Pro Ser Ala Ala Glu Gly Cys Val
             85                  90                  95

Ala Val Val Ala Val Gly Asp Leu Ala Ala Thr Gly Val Arg Ser
            100                 105                 110

Val Ala Glu Lys Leu Gly Leu Pro Phe Phe Tyr Ser Val Pro Ser Pro
            115                 120                 125

Val Tyr Leu Ala Ser Pro His Phe Pro Pro Tyr Asp Glu Pro Thr
            130                 135                 140

Thr Pro Gly Val Thr Asp His Arg Thr Leu Trp Glu Arg Ala His
145                 150                 155                 160

Arg Phe Ala Glu Arg Tyr Gly Glu Thr Leu Asn Arg Arg Ala Ala
                165                 170                 175

Ile Gly Leu Pro Pro Val Glu Asp Val Phe Gly Tyr Gly His Gly Asp
            180                 185                 190

Arg Pro Ile Leu Ser Ala Asp Pro Val Leu Ala Pro Leu Gln Pro Asp
            195                 200                 205

Val Asp Ala Val Gln Thr Gly Ala Trp Ile Leu Thr Asp Asp Arg Pro
210                 215                 220

Leu Pro Pro Glu Leu Glu Ala Phe Leu Ala Ala Gly Pro Pro Pro Val
225                 230                 235                 240

His Val Gly Phe Gly Ser Ser Ser Gly Lys Gly Ile Ala Asp Ala Ala
                245                 250                 255

Lys Ile Ala Val Glu Val Ser Arg Ala His Gly Arg Arg Val Ile Leu
            260                 265                 270

Ser Arg Gly Trp Thr Asp Leu Leu Leu Pro Asp Asp Arg Glu Asp Cys
            275                 280                 285

Phe Ala Ile Gly Glu Val Asn Phe Gln Ala Leu Phe Pro Arg Val Ala
290                 295                 300

Ala Val Ile His His Gly Ser Ala Gly Thr Glu His Val Ala Thr Arg
305                 310                 315                 320

Ala Gly Val Pro Gln Leu Val Ile Pro Arg Asn Thr Asp Gln Pro Tyr
            325                 330                 335

Phe Ala Ala Arg Val Ala Asp Leu Gly Ile Gly Val Ala His Asp Gly
            340                 345                 350

Pro Thr Pro Thr Phe Glu Ser Leu Ser Ala Ala Leu Thr Thr Val Leu
            355                 360                 365

Ala Pro Glu Thr Arg Ala Arg Ala Arg Ala Val Ala Ala Met Ala Gln
            370                 375                 380

Thr Asp Gly Ala Ala Ala Ala Asp Leu Val Leu Ala Ala Val Gly
385                 390                 395                 400

Gly Asn Glu Pro Ala Val Pro Ala
                405

(2) INFORMATION FOR SEQ ID NO:3:

(i) SEQUENCE CHARACTERISTICS:
        (A) LENGTH: 1224 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO
```

(xi) SEQUENCE DESCRIPTION: SEQ ID NO:3:

```
AUGCGUGUGU UGUUGUCGGU GUGCGGAACC CGCGGGGACG UCGAGAUCGC GGUGUCGCUG        60
GCGGUCCGGC UGAAGGCGCU CGGCGUCGGG ACGCGGAUGU GCGCACCGCC CGCCGCCGCC       120
GAGCGGCUGG CCGAGGUCGA GGUGCCGCAU GUGCCGGUCG GCCUUCCGCA GCACAUGAUG       180
UUGCAGGAGG GGAUGCCGCC GCCGCCCCCG GAGGAGGAGC GGCGGCUCGC GGCCAUGACG       240
GUCGAGAUGC AGUUCGACGC GAUCCCCUCG GCCGCCGAAG GAUGCGUGGC GGUGGUGGCG       300
GUCGGCGAUC UGGCCGCCGC GACCGGCGUG CGGUCGGUGG CCGAAAAGCU GGGCCUCCCC       360
UUCUUCUACU CCGUCCCGAG CCCGGUCUAC CUGGCUUCCC CGCACUUCCC GCCGCCCUAU       420
GACGAGCCGA CCACCCCGGG CGUGACCGAC CACCGGACAC UGUGGGAAGA GCGUGCCCAC       480
CGGUUCGCGG AACGGUACGG GGAGACGCUC AACCGGCGGC GGGCCGCGAU CGGCCUGCCG       540
CCGGUGGAGG ACGUCUUCGG CUACGGCCAC GGCGACCGGC CCAUCCUGUC GGCGGACCCG       600
GUCCUCGCCC CGCUGCAGCC GGACGUCGAC GCCGUGCAGA CCGGCGCGUG GAUCCUGACC       660
GACGACCGGC CGCUUCCCCC GGAGCUGGAG GCGUUCCUGG CCGCCGGCCC ACCGCCGGUG       720
CACGUGGGUU UCGGCAGCUC GUCCGGGAAG GGGAUCGCCG ACGCCGCGAA GAUCGCCGUC       780
GAGGUGAGCC GUGCCCACGG CCGCCGGGUG AUCCUCUCCC GAGGGUGGAC CGAUCUGCUC       840
CUGCCCGACG ACCGGGAGGA CUGUUUCGCC AUCGGCGAGG UGAACUUCCA GGCGCUGUUC       900
CCCCGGGUGG CCGCCGUCAU CCAUCACGGC AGCGCGGGCA CGGAACACGU GGCCACGCGG       960
GCGGGCGUCC CCCAGCUCGU GAUCCCCCGG AACACCGACC AGCCGUACUU CGCCGCCAGG      1020
GUUGCCGAUC UGGGGAUCGG UGUGGCGCAC GACGGCCCGA CGCCGACCUU CGAGUCCCUG      1080
UCGGCCGCGC UCACCACGGU CCUGGCGCCG GAAACGCGCG CGCGGGCGCG GGCCGUGGCG      1140
GCCAUGGCCC AGACCGACGG CGCGGCGGCG GCCGCGGAUC UGGUGCUCGC CGCCGUCGGC      1200
GGGAACGAGC CGCCGUUCC CGCG                                             1224
```

GLYCOSYLTRANSFERASE GENE GFTD FROM *AMYCOLATOPSIS ORIENTALIS*

CROSS-REFERENCE

The present application is a divisional of application Ser. No. 08/924,847, filed Sep. 5, 1997 now U.S. Pat. No. 5,821,098 which claims the benefit of provisional application 60/026,028 filed Sep. 13, 1996, now abandoned.

BACKGROUND OF THE INVENTION

This invention relates to recombinant DNA technology. In particular the invention pertains to the cloning of glycosyltransferase gene gtfD from *Amycolatopsis orientalis*, the use of the cloned gene to express and purify the encoded enzyme, and the use of the cloned enzyme in the in vitro production of glycopeptide compounds.

The use of antibiotic compounds has had a profound impact on the practice of medicine in the United States and around the world. Two highly effective antibiotic compounds of the glycopeptide class, vancomycin and teichoplanin, have been approved for use in humans.

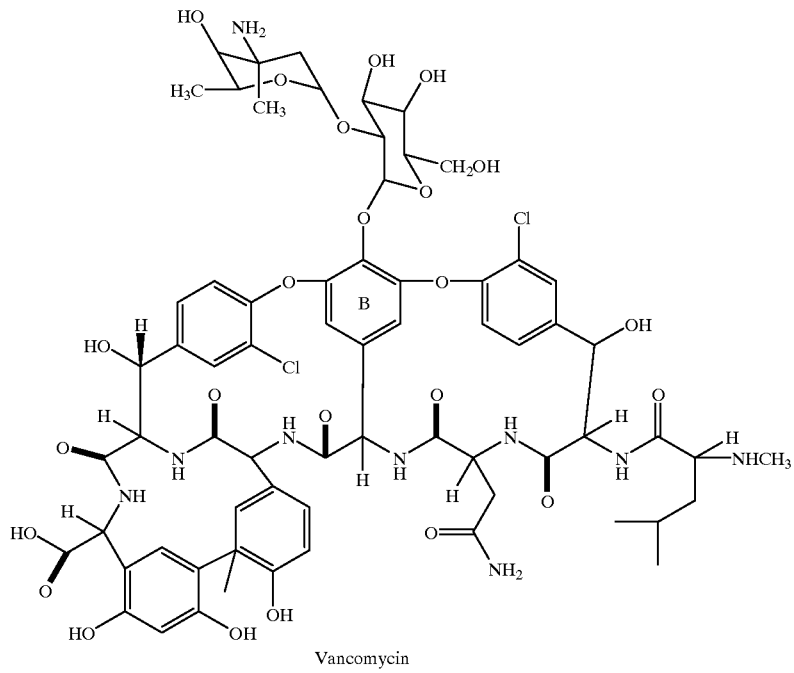

Vancomycin

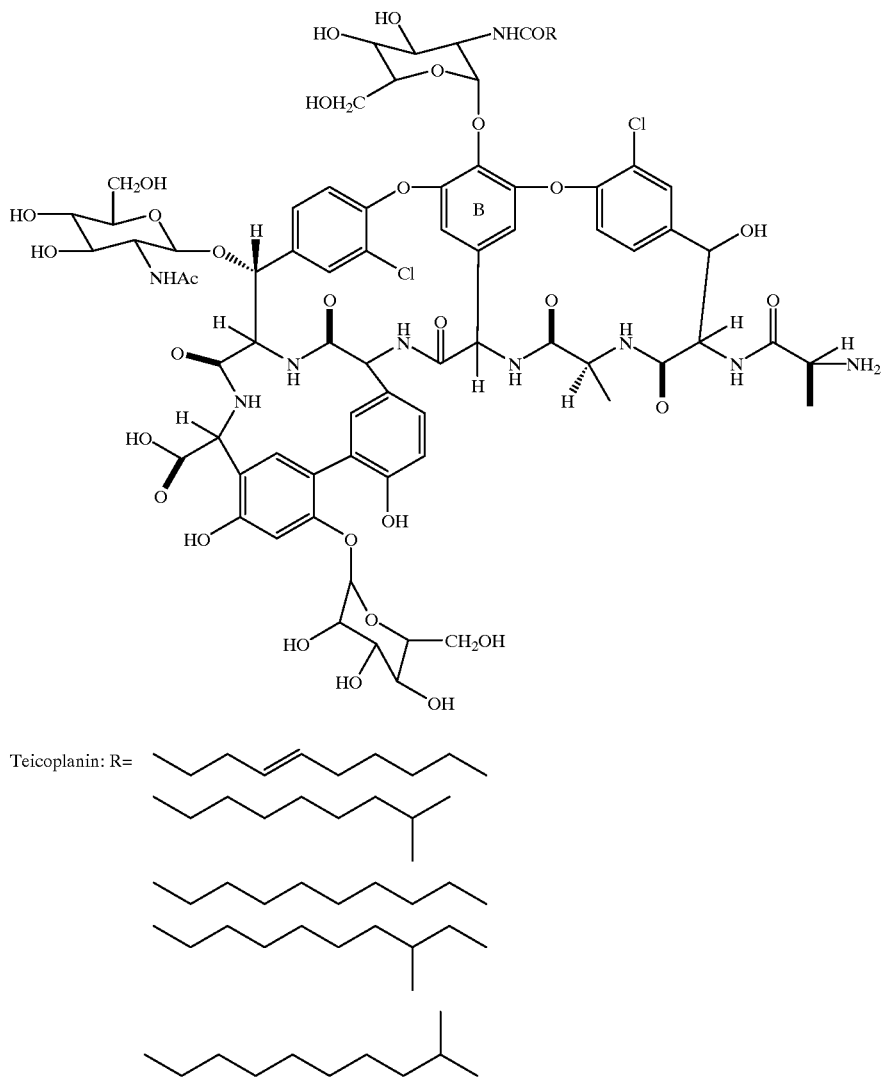

The glycopeptide antibiotics comprise natural and semi-synthetic compounds of highly functionalized linear heptapeptides having a core structure composed of either seven modified or unusual aromatic amino acids, or a mix of aromatic and aliphatic amino acids. Natural glycopeptide compounds have been found in a variety of bacterial genera including Streptomyces, Actinoplanes, Nocardia, Amycolatopsis, Kibdelosporangia, and Pseudonocardia. M. Zmijewski and J. Fayerman. "Glycopeptide Antibiotics," In *Genetics and Biochemistry of Antibiotic Production*, Chap. 18. Ed. L. C. Vining and C. Studtard. Publ. Butterworth Heinemann, Boston (1995). Generally, glycopeptide compounds are differentiated by the placement of sugar substituents on the peptide core. In some instances differentiation arises from the positioning of fatty acid moieties on the sugar substituents. Research has shown that the sugar moieties attached to the core have an effect on the biological activity of glycopeptide molecules.

At present, investigations into glycosylation of glycopeptides and glycopeptide cores are limited to preliminary observations on crude cellular extracts of bacterial strains that produce glycopeptide compounds. These experiments have demonstrated that the glycosylation reaction appears to involve one or more enzymatic activities which attach sugar residues onto a glycopeptide core. One study, for example, demonstrated a glycosylating activity in a crude cellular extract of a vancomycin-producing strain of *Amycolatopsis orientalis*. M. Zmijewski & B. Briggs. "Biosynthesis of vancomycin: identification of TDP-glucose:aglycosylvancomycin glucosyltransferase from *Amycolatopsis orientalis*" FEMS Microbiol. Lett. 59, 129–134 (1989).

The glycosylation of glycopeptide compounds, intrinsically interesting from a scientific point of view, presents a number of practical considerations that warrant continued study of this subject. Recently, a number of glycopeptide resistant strains of pathogenic organisms have been encountered within the clinical environment. This trend toward diminished efficacy of glycopeptide compounds is alarming because of a similar phenomenon in the case of β-lactam antibiotics. It is clear that the rise in antibiotic resistance has occured by a plurality of molecular mechanisms and that resistant organisms possess a diverse repertoire for counteracting the otherwise lethal effect of antibiotic compounds.

In light of the trend toward greater resistance, and in view of the absence of effective alternative treatments, there exists a pressing need to develop new antibiotic compounds. A useful strategy toward this end involves derivitizing presently available glycopeptide compounds by engineering in defined ways the placement and configuration of sugar moieties on the glycopeptide core structure. Achieving molecular rearrangements and substitutions on glycopeptide compounds by chemical means is difficult if not impossible in most cases. By contrast to chemical procedures, enzymatic methods, if available, would provide an effective means to engineer specific modifications onto the glycopeptide core.

The challenge to provide an enzymatic means for modifying glycopeptide core molecules has been met by the present invention. Described herein are gtfD genes isolated from *Amycolatopsis orientalis* encoding glycosyltransferase enzyme GtfD, which adds vancosamine onto the glucose moiety of desvancosaminyl vancomycin.

BRIEF SUMMARY

The present invention is designed to meet the aforementioned need and provides, inter alia, the isolated gtfD gene and other nucleic acid molecules that encode the GtfD gene product from *Amycolatopsis orientalis*. The invention also provides the GtfD protein product of the *Amycolatopsis orientalis* gtfD gene, in substantially purified form.

Having the cloned gtfD gene of *Amycolatopsis orientalis* enables the production of recombinant GtfD protein from which can be made derivatives of glycopeptide compounds in vitro.

In one embodiment the present invention relates to an isolated DNA molecule encoding GtfD protein, said DNA molecule comprising the nucleotide sequence identified as

```
SEQ ID NO. 1:
ATGCGTGTGT TGTTGTCGGT GTGCGGAACC CGCGGGACG TCGAGATCGC GGTGTCGCTG    60

GCGGTCCGGC TGAAGGCGCT CGGCGTCGGG ACGCGGATGT GCGCACCGCC CGCCGCCGCC   120

GAGCGGCTGG CCGAGGTCGA GGTGCCGCAT GTGCCGGTCG GCCTTCCGCA GCACATGATG   180

TTGCAGGAGG GGATGCCGCC GCCGCCCCCG GAGGAGGAGC GGCGGCTCGC GGCCATGACG   240

GTCGAGATGC AGTTCGACGC GATCCCCTCG GCCGCCGAAG GATGCGTGGC GGTGGTGGCG   300

GTCGGCGATC TGGCCGCCGC GACCGGCGTG CGGTCGGTGG CCGAAAAGCT GGGCCTCCCC   360

TTCTTCTACT CCGTCCCGAG CCCGGTCTAC CTGGCTTCCC CGCACTTCCC GCCGCCCTAT   420

GACGAGCCGA CCACCCCGGG CGTGACCGAC CACCGGACAC TGTGGGAAGA GCGTGCCCAC   480

CGGTTCGCGG AACGGTACGG GGAGACGCTC AACCGGCGGC GGGCCGCGAT CGGCCTGCCG   540

CCGGTGGAGG ACGTCTTCGG CTACGGCCAC GGCGACCGGC CCATCCTGTC GGCGGACCCG   600

GTCCTCGCCC CGCTGCAGCC GGACGTCGAC GCCGTGCAGA CCGGCGCGTG GATCCTGACC   660

GACGACCGGC CGCTTCCCCC GGAGCTGGAG GCGTTCCTGG CCGCCGGCCC ACCGCCGGTG   720

CACGTGGGTT TCGGCAGCTC GTCCGGGAAG GGGATCGCCG ACGCCGCGAA GATCGCCGTC   780

GAGGTGAGCC GTGCCCACGG CCGCCGGGTG ATCCTCTCCC GAGGGTGGAC CGATCTGCTC   840

CTGCCCGACG ACCGGGAGGA CTGTTTCGCC ATCGGCGAGG TGAACTTCCA GGCGCTGTTC   900

CCCCGGGTGG CCGCCGTCAT CCATCACGGC AGCGCGGGCA CGGAACACGT GGCCACGCGG   960

GCGGGCGTCC CCCAGCTCGT GATCCCCCGG AACACCGACC AGCCGTACTT CGCCGCCAGG  1020

GTTGCCGATC TGGGGATCGG TGTGGCGCAC GACGGCCCGA CGCCGACCTT CGAGTCCCTG  1080

TCGGCCGCGC TCACCACGGT CCTGGCGCCG GAAACGCGCG CGCGGGCGCG GGCCGTGGCG  1140

GCCATGGCCC AGACCGACGG CGCGGCGGCG GCCGCGGATC TGGTGCTCGC CGCCGTCGGC  1200

GGGAACGAGC CGCCGTTCC CGCG                                          1224
```

In another embodiment the present invention relates to a glycosyltransferase protein molecule, encoded by SEQ ID NO:1 wherein said glycosyltransferase protein molecule comprises the sequence identified as SEQ ID NO. 2.

In a further embodiment the present invention relates to a ribonucleic acid molecule encoding GtfD protein, said ribonucleic acid molecule comprising the sequence identified as SEQ ID NO. 3:

In yet another embodiment, the present invention relates to a recombinant DNA vector which incorporates the *Amycolatopsis orientalis* gtfD gene in operable linkage to gene expression sequences enabling the gtfD gene to be transcribed and translated in a host cell.

In still another embodiment the present invention relates to homologous or heterologous host cells which have been transformed or transfected with the cloned gtfD gene of *Amycolatopsis orientalis* such that the gtfD gene is expressed in the host cell.

In still another embodiment, the present invention relates to a method for producing glycopeptide compounds wherein recombinantly produced GtfD protein is utilized to add one or more sugar moieties onto a glycopeptide.

In a further embodiment the present invention relates to vancomycin which is produced in vitro using recombinant GtfD protein to glycosylate desvancosaminyl vancomycin.

DEFINITIONS

"AGV" denotes aglycosylvancomycin which comprises a vancomycin core having a free hydroxl group on the B ring in place of the disaccharide moiety.

"DVV" denotes desvancosaminyl vancomycin in which a glucose residue is attached onto AGV at the free hydroxl position of the B ring.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

The term "glycopeptide" refers to a functionalized linear heptapeptide compound of natural or semi-synthetic origin, said compound having a core structure.

"Glycopeptide core" or "core" or "core compound" interchangeably denote the progenitor structure of all glycopeptide compounds, comprising either 7 modified or unusual aromatic amino acids, or a mix of aromatic and aliphatic amino acids.

"Glycosylating substrate" refers to a compound which functions as a donor of a sugar moiety in an enzymatic glycosylation reaction, for example, uridine diphosphate-D-glucose.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which two or more strands of nucleic acid join through base pairing with complementary strands. "Selective hybridization" refers to hybridization under conditions of high stringency. The degree of hybridization between nucleic acid molecules varies with the degree of complementarity, the stringency of the hybridization conditions, and the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The gtfD gene of *Amycolatopsis orientalis* encodes a glycosylating enzyme, GtfD. The enzyme will add vancosamine onto the glucose residue of desvancosaminyl vancomycin (DVV) forming vancomycin. The enzyme uses TDP-vancosamine, or UDP-vancosamine as the glycosylating substrate.

The gtfD gene of *Amycolatopsis orientalis* comprises a DNA sequence of 1224 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product identified as SEQ ID NO:2. All such substitutions are intended to be within the scope of the invention.

Gene Isolation Procedures

Those skilled in the art will recogize that the gtfD gene may be obtained by a plurality of applicable techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the gtfD gene of *Amycolatopsis orientalis* or fragment thereof could also be isolated by PCR amplification of *Amycolatopsis orientalis* genomic DNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990), which hereby is incorporated by reference. The PCR amplification, which comprises genomic DNA, suitable enzymes, primers, and buffers, is conveniently carried out in a DNA Thermal Cycler (Perkin Elmer Cetus, Norwalk, Conn.). A positive PCR amplification is determined by detecting an appropriately-sized DNA fragment following agarose gel electrophoresis.

Protein Production Methods

One embodiment of the present invention relates to the substantially purified protein GtfD identified as SEQ ID NO:2 and encoded by the gtfD gene or functionally related proteins of *Amycolatopsis orientalis*.

Skilled artisans will recognize that the proteins of the present invention can be synthesized or purified by any number of suitable methods. For example, the amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and are described in a number of general texts on the subject. See, e.g., H. Dugas and C. Penney, *Bioorganic Chemistry* (1981) Springer-Verlag, New York, 54–92. For example, peptides may be synthesized by solid-phase methodology using an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably –20_C. for thirty minutes followed by thirty minutes at 0_C.

The proteins of the present invention can also be produced by recombinant DNA methods using the cloned gtfD gene of *Amycolatopsis orientalis*. Recombinant methods are preferred if a high yield is desired. Expression of the cloned gtfD gene can be carried out in a variety of suitable host cells well known to those skilled in the art. The gtfD gene is introduced into a host cell by any suitable transformation, transfection, or conjugation means, well known to those skilled in the art. While chromosomal integration of the cloned gtfD gene is within the scope of the present invention, it is preferred that the gene be cloned into a suitable extra-chromosomally maintained expression vector so that the coding region of the gtfD gene is operably linked to a constitutive or inducible promoter.

The basic steps in the recombinant production of the GtfD protein are:
 a) constructing a natural, synthetic or semi-synthetic DNA encoding GtfD protein;
 b) integrating said DNA into an expression vector in a manner suitable for expressing the GtfD protein, either alone or as a fusion protein;
 c) transforming, transfecting, or otherwise introducing said expression vector into an appropriate eukaryotic or prokaryotic host cell to form a recombinant host cell,
 d) culturing said recombinant host cell under conditions that favor expression of the GtfD protein; and
 e) recovering and purifying the GtfD protein by any suitable means.

Expressing Recombinant GtfD Protein in Procaryotic and Eucaryotic Host Cells

In general, prokaryotes are used for cloning DNA and for constructing the vectors of the present invention. Prokaryotes are also employed in the production of the GtfD protein. For example, the *Escherichia coli* K12 strain 294 (ATCC No. 31446) is particularly useful for the expression of foreign proteins. Other strains of *E. coli*, bacilli such as *Bacillus subtilis*, enterobacteriaceae such as *Salmonella typhimurium* or *Serratia marcescans*, various Pseudomonas species, and other bacteria, such as Streptomyces, may also be employed as host cells in the cloning and expression of the recombinant proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system (vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized by recombinant or chemical means as the amino acid sequence identified as SEQ ID NO:2, or as a fusion protein comprising the protein of interest and another protein or peptide which may be removable by enzymatic or chemical cleavage. Expression as a fusion protein may prolong the lifespan, increase the yield of the desired peptide, or provide a convenient means for purifying the protein. A variety of peptidases (e.g. enterokinase and thrombin) which cleave a polypeptide at specific sites are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to prokaryotes, mammalian host cells and eukaryotic microbes such as yeast may also be used to isolate and express the genes of the present invention. The simple eucaryote *Saccharomyces cerevisiae*, is the most commonly used eukaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced GtfD Protein

An expression vector carrying the cloned gtfD gene of *Amycolatopsis orientalis* is transformed, transfected, or otherwise introduced into a suitable host cell using standard methods. Cells which contain the vector are propagated under conditions suitable for expression of the Glycosyltransferase protein. If the gtfD gene is under the control of an inducible promoter, growth media and other conditions should incorporate the appropriate inducer.

The recombinantly produced protein may be purified from cellular extracts of transformed cells by any suitable means. In a preferred protein purification method, the gtfD gene is modified at the 5' end to incorporate several histidine residues at the amino terminus of the GtfD protein product. The "histidine tag" enables a single-step protein purification method referred to as "immobilized metal ion affinity chromatography" (IMAC), essentially as described in M. C. Smith et al. "Chelating Peptide-immobilized metal-ion affinity chromatography," Chapter 12, in *Protein Purification: From Molecular Mechanisms to Large Scale Processes*, American Chemical Society, Washington, D.C. (1990), and in U.S. Pat. No. 4,569,794 both of which hereby are incorporated by reference. The IMAC method enables rapid isolation of substantially pure protein.

The gtfD gene, which comprises nucleic acid encoding SEQ ID NO:2, may also be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the gtfD gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. For example, the nucleic acid compounds of the present invention may be used to hybridize to genomic DNA which has been digested with one or more restriction enzymes and separated on an electrophoretic gel. The hybridization of radiolabeled probes onto such restricted DNA, usually fixed to a membrane after electrophoresis, is well known in the art. See, e.g., J. Sambrook, supra. A compound which comprises SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Amycolatopsis orientalis* DNA or mRNA encoding gtfD, is provided. Preferably, the 18 or more base pair compound is DNA. The probes and primers of this invention can be prepared by techniques well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1. Plasmid pCZA366 is an especially preferred DNA vector of the present invention.

Choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers and metabolic markers), and the desired number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. A number of inducible promoters responding to a variety of induction signals are available, for example, carbon source, metal ions, and heat. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. A preferred host cell is any strain of *E. coli* which can accomodate high level expression of a gene(s) introduced by transformation or transfection. Preferred vectors for expression are those which comprise SEQ ID NO:1. An especially preferred expression vector for use in *E. coli* is plasmid pCZA366, which comprises SEQ ID NO:1. Transformed host cells may be cultured under conditions well known to skilled artisans such that SEQ ID NO:2 is expressed, thereby producing GtfD protein in the recombinant host cell.

The cloned GtfD enzyme is useful for glycosylating glycopeptide compounds in vitro. A method embodied herein comprises glycosylating a glycopeptide compound by contacting the glycopeptide with the cloned GtfD protein and monitoring the glycopeptide compound that is produced.

The instant invention provides an enzymatic method for the in vitro glycosylation of DVV using the cloned *A. orientalis* gtfD gene, said method comprising the steps of:

a) expressing the cloned gtfD gene in a host cell so that GtfD enzyme is produced;

b) exposing said GtfD enzyme to a glycopeptide compound, in vivo or in vitro;

c) introducing a suitable glycosylating substrate; and d) characterizing and/or purifying the product glycopeptide by any suitable means.

The method can be adapted to substantially purified recombinant GtfD protein, as described herein, or to a crude cellular extract isolated from a recombinant cell culture that expresses the GtfD protein by virtue of having been transformed, transfected, or otherwise endowed with the gtfD gene.

A suitable substrate for the in vitro glycosylation reaction comprises TDP-vancosamine. This substrate can be obtained by acid-catalyzed hydrolysis of vancomycin using any suitable method known to skilled artisans (See e.g. M. Sim et al. "Synthesis and use of glycosyl phosphites: an effective route to glycosyl phophates, sugar nucleotides, and glycosides" J. Am. Chem. Soc. 115, 2260–67 (1993)). In one method for preparation of this substrate, following acid hydrolysis of vancomycin, the hydrolytic products are condensed with dibenzyl N,N-diethylphosphoramidite as a phosphitylating reagent so as to generate the appropriate dibenzyl glycosyl phosphite derivative. Oxidation and deprotection, followed by reaction with thymidine 5'-monophospho-morpholidate provides the desired sugar substrate.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Amycolatopsis orientalis* Gene gtfD in *Escherichia coli*

Plasmid pCZA366 is an approximately 7 kilobasepair expression vector suitable for expressing the gtfD gene at high levels in a procaryotic host, for example *E. coli*. Plasmid pCZA366 is derived from parent plasmid PET-11a (obtained from Novagen, Madison, Wis.), which contains an origin of DNA replication (ori), an ampicillin resistance gene (Amp), the T7 promoter region, and the lacI gene for repressing the lac operon.

The gtfD gene cassette inserted into pCZA366 is generated by the PCR carried out on *A. orientalis* C329.4 genomic DNA using standard conditions. Primers used in the amplification reaction are complementary to the 5' and 3' ends of the gtfD gene sequence specified in SEQ ID NO: 1 and are engineered to contain NdeI and BglII restriction sites. The PCR-amplified gtfD gene sequence is digested with NdeI and BglII and ligated into pET11a, which has been digested with NdeI and BamHI.

EXAMPLE 2

Transformation of *Escherichia coli* with an Expression Plasmid Carrying the gtfD gene of *Amycolatopsis orientalis*

Plasmid pCZA366 is transformed into *E. coli* BL21(DE3) (hsdS gal λcIts857 ind1Sam7nin5lacUV5-T7gene 1) using standard methods (See e.g. Sambrook et al. Supra).

EXAMPLE 3

In Vitro Glycosylation of Desvancosaminyl Vancomycin Using Cloned gtfD Gene

Approximately 25 ml of a culture of *E. coli* BL21(DE3) cells transformed with plasmid pCZA366 is grown to an $OD_{600}$ of about 0.6: Induction of gtfD gene expression is effected by adding 1 mM IPTG with shaking at room temperature for 2 to 3 hours. Thereafter, cells from about 20 ml of the induced culture are pelleted by centrifugation and resuspended in 2 ml of 50 mM Tris pH 9.0, 100 μg/ml lysozyme with incubation on ice for 10 minutes to effect cell lysis. After cell lysis the suspension is passed through a 23-gauge syringe and centrifuged at 10,000×g for 15 minutes to pellet cell debris. The resulting cell extract is used for the glycosylation reaction.

The 1 ml glycosylation reaction contained:

1 mg DVV in 50 mM Tris HCL, pH 9.0

5 mg TDP-vancosamine 1 mg bovine serum albumin (BSA)

20 μl 1 M MgCl2

20 μl 1 M CaC12

5 μl 1 M dithiothreitol (DTT)

445 μl cell extract

Distilled water to 1 ml.

A control reaction contained cell extract from non-transformed BL21(DE3). After incubation overnight at 37_C. with slight shaking the reaction is filtered through a 0.45 micron filter and analyzed by HPLC.

We claim:

1. A substantially pure glycosyltransferase protein from *Amycolatopsis orientalis* having the amino acid of SEQ ID NO 2.

* * * * *